(12) United States Patent
Wang et al.

(10) Patent No.: US 8,633,343 B2
(45) Date of Patent: Jan. 21, 2014

(54) TRANSALKYLATION OF POLYCYCLOHEXYLBENZENES

(75) Inventors: Kun Wang, Bridgewater, NJ (US); Jane C. Cheng, Bridgewater, NJ (US); Terry E. Helton, Bethlehem, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 48 days.

(21) Appl. No.: 13/264,464

(22) PCT Filed: Apr. 14, 2010

(86) PCT No.: PCT/US2010/031029
§ 371 (c)(1),
(2), (4) Date: Nov. 9, 2011

(87) PCT Pub. No.: WO2010/138248
PCT Pub. Date: Dec. 2, 2010

(65) Prior Publication Data
US 2012/0046499 A1    Feb. 23, 2012

Related U.S. Application Data

(60) Provisional application No. 61/181,133, filed on May 26, 2009.

(51) Int. Cl.
*C07C 2/66*    (2006.01)
*C07C 37/08*    (2006.01)

(52) U.S. Cl.
USPC .......................... 585/375; 585/475; 568/798

(58) Field of Classification Search
USPC .................................. 585/375, 475
See application file for complete search history.

(56) References Cited

U.S. PATENT DOCUMENTS

| | | | |
|---|---|---|---|
| 3,308,069 A | 3/1967 | Wadlinger et al. | |
| 3,760,017 A * | 9/1973 | Arkell et al. | 585/268 |
| 3,766,093 A | 10/1973 | Chu | |
| 3,956,183 A | 5/1976 | Zuech | |
| 3,984,490 A | 10/1976 | Chung et al. | |
| 4,094,918 A | 6/1978 | Murtha et al. | |
| 4,122,125 A | 10/1978 | Murtha et al. | |
| 4,152,361 A | 5/1979 | Imai | |
| 4,177,165 A | 12/1979 | Murtha et al. | |
| 4,206,082 A | 6/1980 | Murtha et al. | |
| 4,237,329 A | 12/1980 | Kamiyama et al. | |
| RE30,726 E | 9/1981 | Otten et al. | |
| 4,439,409 A | 3/1984 | Puppe et al. | |
| 4,599,470 A | 7/1986 | Gregory et al. | |
| 4,826,667 A | 5/1989 | Zones et al. | |
| 4,954,325 A | 9/1990 | Rubin et al. | |
| 5,053,571 A | 10/1991 | Makkee | |
| 5,091,241 A | 2/1992 | Lang et al. | |
| 5,236,575 A | 8/1993 | Bennett et al. | |
| 5,250,277 A | 10/1993 | Kresge et al. | |
| 5,308,668 A | 5/1994 | Tsuji | |
| 5,326,697 A | 7/1994 | Magers | |
| 5,510,309 A | 4/1996 | Chang et al. | |
| 5,786,050 A | 7/1998 | Otsuka et al. | |
| 6,037,513 A | 3/2000 | Chang et al. | |
| 6,489,529 B1 | 12/2002 | Cheng et al. | |
| 7,241,930 B2 | 7/2007 | Schlosberg et al. | |
| 7,501,547 B2 | 3/2009 | Clark et al. | |
| 2008/0242905 A1 | 10/2008 | Clark et al. | |
| 2008/0242907 A1 | 10/2008 | Clark et al. | |
| 2008/0281137 A1 * | 11/2008 | Clark et al. | 585/470 |
| 2011/0015457 A1 * | 1/2011 | Cheng et al. | 585/268 |
| 2011/0288341 A1 * | 11/2011 | Chen et al. | 568/365 |

FOREIGN PATENT DOCUMENTS

| | | |
|---|---|---|
| EP | 0 439 632 | 8/1991 |
| EP | 0 538 518 | 4/1993 |
| WO | 95/07874 | 3/1995 |
| WO | 96/20148 | 7/1996 |
| WO | 2006/107462 | 10/2006 |
| WO | 2009/021604 | 2/2009 |
| WO | 2010/138248 | 12/2010 |

OTHER PUBLICATIONS

Farcasiu et al., "*Transalkylation of Polycyclic Aromatics Catalyzed by Trifluoromethanesulfonic Acid*", Energy and Fuels, 1987, vol. 1, pp. 28-31.

\* cited by examiner

*Primary Examiner* — Brian J Davis
(74) *Attorney, Agent, or Firm* — Jamie L. Sullivan; Siwen Chen

(57) ABSTRACT

In a process for the transalkylation of polycyclohexylbenzenes, a feed containing at least one polycyclohexylbenzene is contacted with benzene under transalkylation conditions with a catalyst comprising a zeolite USY having a silica to alumina molar ratio in excess of 10 to convert at least part of said polycyclohexylbenzene to cyclohexylbenzene.

16 Claims, No Drawings

TRANSALKYLATION OF POLYCYCLOHEXYLBENZENES

CROSS REFERENCE TO RELATED APPLICATIONS

This application is a National Stage Application of International Application No. PCT/US2010/031029 filed Apr. 14, 2010, which claims the benefit of prior U.S. provisional application Ser. No. 61/181,133 filed May 26, 2009, both of which are hereby incorporated by reference in their entirety.

FIELD

The present invention relates to a process for the transalkylation of polycyclohexylbenzenes into monocyclhexylbenzene and to the use of the resultant monocyclohexylbenzene in the production of phenol and cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene.

Thus, a process that uses higher alkenes instead of propylene as feed and coproduces higher ketones, such as cyclohexanone, rather than acetone may be an attractive alternative route to the production of phenols. For example, there is a growing market for cyclohexanone, which is used as an industrial solvent, as an activator in oxidation reactions and in the production of adipic acid, cyclohexanone resins, cyclohexanone oxime, caprolactam and nylon 6.

It is known from U.S. Pat. No. 5,053,571 that cyclohexylbenzene can be produced by contacting benzene with hydrogen in the presence of a catalyst comprising ruthenium and nickel supported on zeolite beta and that the resultant cyclohexylbenzene can be processed in two steps to cyclohexanone and phenol. Similarly, U.S. Pat. No. 6,037,513 discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. The '513 patent also discloses that the resultant cyclohexylbenzene can be oxidized to the corresponding hydroperoxide and the peroxide decomposed to the desired phenol and cyclohexanone.

One problem facing the commercial exploitation of these methods of producing cyclohexylbenzene is that generally around 20 wt % of the products of the hydroalkylation process are di- and tri-cyclohexylbenzenes. For the overall process to be economically feasible, it is therefore necessary to convert these polycyclohexylbenzenes into additional useful monocyclohexylbenzene product.

One possible solution to this problem is to transalkylate the polycyclohexylbenzenes with additional benzene, a solution which is addressed in the '513 patent by effecting the transalkylation in the presence of a catalyst containing the same molecular sieve as used in the hydroalkylation catalyst, namely an MCM-22 family catalyst, but in the absence of the metal components on the hydroalkylation catalyst and in the absence of a hydrogen co-feed.

In addition, U.S. Pat. No. 6,489,529 discloses that dicyclohexylbenzene can be converted to the monoalkylated derivative by contacting the dicyclohexylbenzene with benzene in the presence of a catalyst selected from the group consisting of an acidic solid comprising Group IVB metal oxide modified with an oxyanion of a Group VIB metal oxide, TEA-mordenite, and zeolite beta.

In our co-pending PCT Application No. PCT/EP 2008/006072 we have described a process for producing cyclohexylbenzene where dicyclohexylbenzene by-product is transalkylated with additional benzene in a transalkylation reactor, normally separate from the hydroalkylation reactor, over a suitable transalkylation catalyst, such as a molecular sieve of the MCM-22 family, zeolite beta, MCM-68 (see U.S. Pat. No. 6,049,018), zeolite X, zeolite Y, zeolite USY, and mordenite.

The silica/alumina molar ratio of a given zeolite is often variable. For example, certain faujasite zeolites can have varying silica/alumina ratios such as zeolite X which can be synthesized with silica/alumina molar ratios of from 1.5:1 up to 3:1, while that ratio in zeolite Y is from 3:1 to 6:1. In the ultrastable Y zeolite (zeolite USY), which is made by dealuminating zeolite Y, the silica/alumina ratio can be made to exceed the value of 6:1 typical for zeolite Y. The term dealuminating is generally understood to mean the removal of aluminum from the zeolite framework, even where the overall composition of the material is unaltered or only slightly altered because the aluminum removed from the framework remains in the channels and cavities.

For any catalyst to be viable for the commercial scale transalkylation of polycyclohexylbenzenes, the catalyst must not only exhibit significant activity in the conversion of the polyalkylated species but must also selectively produce the desired monocyclohexylbenzene product rather than unwanted by-products. In particular, it is important to minimize the production of methylcyclopentylbenzene since the latter can be difficult to separate from the desired monocyclohexylbenzene product and produces heavy alcohols and ketones in the subsequent oxidation stage.

According to the present invention, it has now been found that certain forms of zeolite USY exhibit a unique combination of a high activity for the conversion of polycyclohexylbenzenes with a high selectivity for the desired monocyclohexylbenzene product and a low selectivity for the unwanted methylcyclopentylbenzene impurity.

SUMMARY

In one aspect, the invention resides in a process for the transalkylation of polycyclohexylbenzenes, the process comprising contacting a feed containing at least one polycyclohexylbenzene with benzene under transalkylation conditions with a catalyst comprising a zeolite USY having a silica to alumina molar ratio in excess of 10 to convert at least part of said polycyclohexylbenzene to cyclohexylbenzene.

Conveniently, the zeolite USY has a silica to alumina molar ratio in excess of 25.

Conveniently, the zeolite USY has a silica to alumina molar ratio in excess of 50 and typically has a unit cell size less than or equal to 24.50.

Conveniently, said transalkylation conditions include a temperature of about 100° C. to about 300° C., a pressure of about 350 kPA to about 4200 kPa, and a benzene to polycyclohexylbenzene molar ratio of about 1:1 to about 50:1.

In one embodiment, the feed comprises at least part of an effluent produced by a method comprising contacting benzene and hydrogen under hydroalkylation conditions with a catalyst comprising a hydrogenation metal and a molecular sieve selected from zeolite beta, zeolite X, zeolite Y, mordenite, and a molecular sieve of the MCM-22 family.

In a further aspect, the invention resides in a process for producing cyclohexylbenzene, the process comprising:
(a) contacting benzene and hydrogen with a first catalyst under hydroalkylation conditions to produce an effluent containing cyclohexylbenzene and polycyclohexylbenzenes;
(b) separating cyclohexylbenzene from said effluent; and
(c) reacting at least part of the polycyclohexylbenzenes from said effluent with benzene under transalkylation conditions with a second catalyst comprising a zeolite USY having a silica to alumina molar ratio in excess of 10 to convert at least part of said polycyclohexylbenzenes to cyclohexylbenzene.

In yet a further aspect, the invention resides in a process for producing phenol and cyclohexanone, the process comprising:
(a) contacting benzene and hydrogen with a first catalyst under hydroalkylation conditions to produce an effluent containing cyclohexylbenzene and polycyclohexylbenzenes;
(b) separating cyclohexylbenzene from said effluent;
(c) reacting at least part of the polycyclohexylbenzenes from said effluent with benzene under transalkylation conditions with a second catalyst comprising a zeolite USY having a silica to alumina molar ratio in excess of 10 to convert at least part of said polycyclohexylbenzene to cyclohexylbenzene;
(d) oxidizing at least part of the cyclohexylbenzene from (b) and (c) to produce cyclohexylbenzene hydroperoxide; and
(e) cleaving at least part of the cyclohexylbenzene hydroperoxide to produce phenol and cyclohexanone.

Conveniently, the first catalyst comprises a hydrogenation metal and a molecular sieve selected from zeolite beta, zeolite X, zeolite Y, mordenite and a molecular sieve of the MCM-22 family.

DETAILED DESCRIPTION OF THE EMBODIMENTS

Described herein is a process for the transalkylation of polycyclohexylbenzenes and, particularly, but not exclusively, the polycyclohexylbenzenes produced as a by-product of the catalytic hydroalkylation of benzene. Thus the catalytic hydroalkylation of benzene is a useful route to the production of cyclohexylbenzene, which in turn can be used a precursor in the manufacture of phenol and cyclohexanone. However, as will be discussed below, current methods for catalytic hydroalkylation of benzene produce about 20% of di- and tricyclohexylbenzenes by weight of the hydroalkylated product. Thus, to be commercially viable, any method of producing phenol and cyclohexanone via the catalytic hydroalkylation of benzene requires an effective method for transalkylation of polycyclohexylbenzenes to additional monocyclohexylbenzene product.

Polycyclohexylbenzenes comprise di-cyclohexylbenzene and tricyclohexylbenzene.

Benzene Hydroalkylation

The catalytic hydroalkylation of benzene involves contacting benzene with hydrogen under hydroalkylation conditions in the presence of a suitable hydroalkylation catalyst whereby the benzene undergoes the following reaction:

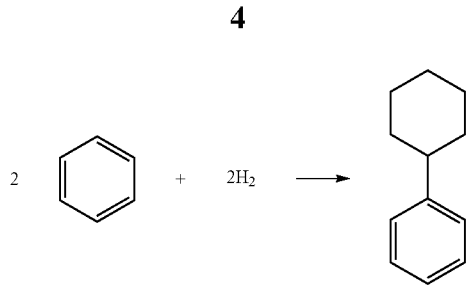

Competing reactions include the complete saturation of the benzene to produce cyclohexane (CHB), polyalkylation to produce dicyclohexylbenzene and tricyclohexylbenzene and reorganization/alkylation reactions to produce impurities, such as methylcyclopentylbenzene. The major competing reaction is polyalkylation since, even with the most selective catalysts, such as the MCM-22 family zeolites disclosed herein, the reaction effluent contains 20% or more of dicyclohexylbenzene and tricyclohexylbenzene by weight of the converted products.

Any commercially available benzene feed can be used in the hydroalkylation step, but preferably the benzene has a purity level of at least 99 wt %. Similarly, whereas the source of hydrogen is not critical, it is generally desirable that the hydrogen is at least 99% pure.

Conveniently, the total feed to the hydroalkylation step contains less than 1000 ppm, such as less than 500 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

The hydroalkylation reaction can be conducted in a wide range of reactor configurations including fixed bed, slurry reactors, and/or catalytic distillation towers. Suitable reaction temperatures are between about 100° C. and about 400° C., such as between about 125° C. and about 250° C., while suitable reaction pressures are between about 100 and about 7,000 kPaa, such as between about 500 and about 5,000 kPaa. Suitable values for the molar ratio of hydrogen to benzene are between about 0.15:1 and about 15:1, such as between about 0.4:1 and about 4:1.

The catalyst employed in hydroalkylation reaction may be a composite of a molecular sieve, an inorganic oxide different from the molecular sieve and a hydrogenation metal, preferably in which at least 50 wt % of the hydrogenation metal is supported on the inorganic oxide rather than on the molecular sieve. In particular, it is found that by supporting the hydrogenation metal on the inorganic oxide, the activity of the catalyst and its selectivity to cyclohexylbenzene and dicyclohexylbenzene is increased as compared with an equivalent catalyst in which the hydrogenation metal is supported on the molecular sieve.

Generally, the molecular sieve employed in the hydroalkylation process has pore system including at least one channel defined by a 12-membered ring of tetrahedrally coordinated atoms. Examples of such molecular sieves include zeolite beta, zeolite X, zeolite Y, mordenite and MCM-68.

Alternatively, the hydroalkylation catalyst includes at least one molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

The inorganic oxide employed in the hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63 (5), 27 (1985).

Similarly, any known hydrogenation metal can be employed in the hydroalkylation catalyst composite although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal is present in the composite catalyst such that at least 50 wt %, for example at least 75 wt %, and generally substantially all of the hydrogenation metal is supported on the inorganic oxide. This is conveniently achieved by depositing at least part of the hydrogenation metal on the inorganic oxide, for example by incipient wetness impregnation, before the metal-containing inorganic oxide is composited with said molecular sieve. If necessary, additional hydrogenation metal can subsequently be deposited on the resultant catalyst composite. Typically, the catalyst composite is produced by co-pelletization, in which a mixture of the molecular sieve and the inorganic oxide are formed into pellets at high pressure (generally about 350 to about 350,000 kPa), or by co-extrusion, in which a slurry of the molecular sieve and the inorganic oxide, optionally together with a separate binder, are forced through a die.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Transalkylation of Polycyclohexylbenzenes

The major components of the effluent from the hydroalkylation reaction are the desired cyclohexylbenzene product, unreacted benzene and di- and tricyclohexylbenzene. The unreacted benzene is normally recovered by distillation and recycled to the hydroalkylation reactor. The bottoms from the benzene distillation are further distilled to separate the monocyclohexylbenzene product from any polycyclohexylbenzenes and other heavies. The polycyclohexylbenzenes must then be transalkylated with additional benzene to maximize the production of the desired monoalkylated species. The present process provides a novel and advantageous method of effecting this transalkylation.

In particular, the present transalkylation process involves reacting the polycyclohexylbenzenes with additional benzene, either fresh benzene or unreacted benzene from the hydroalkylation step, in the presence of a catalyst comprising a dealuminated zeolite Y (i.e. zeolite USY) having a silica to alumina molar ratio in excess of 10, typically a silica to alumina molar ratio in excess of 25 and typically a silica to alumina molar ratio in excess of 50. Conveniently, the catalyst comprises a zeolite USY having a silica to alumina molar ratio in excess of 25 and a unit cell size less than or equal to 24.50, typically less than or equal to 24.26.

In other embodiments, the transalkylation catalyst has a silica to alumina molar ratio of from 10 to 1,000 or from 10 to 500 or from 10 to 100 or from 25 to 1,000 or from 25 to 500 or from 25 to 100 or from 50 to 1,000 or from 50 to 500 or from 50 to 100. In other embodiments, the silica to alumina lower limit may be 10, 15, 20, 25, 30, 35, 40, 45, 50; and the silica to alumina upper limit may be 75, 125, 150, 175, 200, 250, 300, 400, 500, 600, 700, 800, 900, 1,000, 2,000, 3,000, 4,000, and 5,000 with ranges from any lower limit to any upper limit being contemplated.

In one embodiment, the transalkylation catalyst has an alpha value of less than 100, such as less than 75, typically less than 50. In this respect, the alpha value is an approximate indication of the catalytic cracking activity of a material as compared to a standard catalyst. It gives the relative rate constant of the material for hexane cracking (rate of normal hexane conversion per volume of catalyst per unit time) compared to the activity of a standard silica-alumina cracking catalyst taken as an Alpha of 1 (Rate Constant=0.016 sec-1). The Alpha Test is described in U.S. Pat. No. 3,354,078; in the *Journal of Catalysis,* 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis,* 61, 395 (1980).

In one embodiment, the transalkylation catalyst has a BET surface area greater than 500 m$^2$/g, typically greater than 600 m$^2$/g and a pore volume greater than 0.5 cc/g, typically greater than 0.7 cc/g.

The transalkylation catalyst may comprise a binder, such as those described above for the hydroalkylation catalyst, or alternatively can be binder-free. The transalkylation catalyst is generally free of any hydrogenation metal.

The transalkylation process is typically conducted in a transalkylation reactor, separate from the hydroalkylation reactor, under at least partial liquid phase conditions, which suitably include a temperature of about 100 to about 300° C., a pressure of about 350 kPA to about 4200 kPa, a weight hourly space velocity of about 0.5 to about 50 hr$^{-1}$ on total transalkylation feed, and a benzene to polycyclohexylbenzene molar ratio of about 1:10 to about 50:1. In one embodiment, conditions include a temperature of about 150 to about 250° C., a pressure of about 700 kPA to about 3500 kPa, a weight hourly space velocity of about 1 to about 30 hr$^{-1}$ on total transalkylation feed, and a benzene to polycyclohexylbenzene molar ratio of about 1:1 to about 15:1. In still another embodiment, conditions include a temperature of about 150 to about 200° C., a pressure of about 1500 kPA to about 3000 kPa, and a benzene to polycyclohexylbenzene molar ratio of about 1:1, about 1:2, about 1:3, about 1:4, about 1:5, about 1.5:2.5, about 1.5:3.5, and about 1.5:4.5.

It is important in the transalkylation step to achieve significant conversion of the polycyclohexylbenzenes to the monoalkylated product, while at the same time minimizing methylcyclopentalbenzene (MCPB) and heavies (C$_{18}$+) formation. Presence of MCPB in the products can cause problems for the steps further down the process in that certain isomers of MCPB can also be oxidized and cleaved leading formation of methylcyclopentanone, which has to be separated from cyclohexanone. Further, the 1-methyl-1-phenyl cyclopentane isomer cannot be separated from CHB by distillation and will not be oxidized in the oxidation step, thereby building up in concentration in the recycle streams. Heavy products (C$_{18}$+) will end up in the phenol tar due to their high boiling points, resulting in materials loss.

In addition, since the transalkylation catalyst will slowly lose activity primarily due to build up of coke, it is important that the aging rate of the catalyst is as low as possible (thereby allowing long cycle times between regenerations). In addition, since catalyst regeneration to remove coke normally involves burning of the coke in the presence of air, either ex-situ or in-situ, it is also important that the catalyst can readily be regenerated with a little loss in activity as possible.

Using the present transalkylation process, with a high silica zeolite USY as the catalyst, it is found to be possible to achieve polycyclohexylbenzene conversion rates in excess of 50% with a selectivity to monocyclohexylbenzene greater than 90 wt % and a selectivity to methylcyclopentylbenzene less than 1.5 wt %. In contrast, as will be shown in the following Examples, using other zeolite transalkylation catalysts, it is found that at least one of the conversion and selectivity values are adversely affected. In addition, the high silica zeolite USY employed in the present transalkylation process appears to exhibit slow catalyst aging and good regeneration stability.

Cyclohexylbenzene Oxidation

The major components of the effluent from the transalkylation reaction are the desired cyclohexylbenzene product, unreacted benzene and unreacted di- and tricyclohexylbenzene. The unreacted benzene is normally recovered by distillation, typically in the same unit used to separate the unreacted benzene in the hydroalkylation effluent. The bottoms from the benzene distillation are further distilled to separate the monocyclohexylbenzene product from unreacted polycyclohexylbenzenes and other heavies. The unreacted polycyclohexylbenzenes can then be recycled to the transalkylation, whereas the monocyclohexylbenzene can be combined with CHB recovered from the hydroalkylation step. The combined CHB product can then be marketed as a commodity chemical but more generally is directly converted into phenol and cyclohexanone.

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction can conveniently be conducted in a CSTR reactor or a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component. Typical basic components that can be used are alkali metal carbonate, bicarbonate, hydroxide, or phenoxide, as well as ammonia or organic amines. When an aqueous solution of the basic component is used for neutralization, the salt-enriched aqueous phase is subsequently separated from the organic phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species.

EXAMPLES

The invention will now be more particularly described with reference to the following non-limiting Examples.

In the Examples, the following screening procedure was followed to test catalysts for transalkylation of dicyclohexylbenzene with benzene. One gram of catalyst in the 20-40 mesh size range was diluted with sand to a volume of 3 cc and charged to a fixed-bed reactor with 0.375 inch (0.95 cm) outside diameter. The catalyst was dried in the reactor with 100 cc/min flowing $N_2$ at 125° C. and 1 atmosphere pressure for 2 hours. Nitrogen was turned off and the reactor pressure was set to 300 psig (2170 kPa).

Commercial benzene was percolated through a column of alumina to remove trace water, oxygenates, and other trace N- or S-containing impurities before use. A feed containing 75% of the pre-treated benzene and 25% p-dicyclohexylbenzene (DCHB) by weight was then introduced to the reactor via an ISCO pump at 60 cc/h for 1 hour while the reactor was heated to the desired temperature. The feed rate was reduced to 4.5 cc/h (WHSV=4) and the test began. Liquid products were collected in a chilled trap and analyzed by gas chromatography off-line.

Example 1

DCHB/Benzene Transalkylation Over $WO_x/ZrO_2$ (Comparative)

One gram of mixed metal oxides $WO_x/ZrO_2$ was used in testing DCHB/benzene transalkylation following procedure described above. A product sample was taken after 26 hours on stream and the results are shown in Table 1.

Example 2

DCHB/Benzene Transalkylation Over Alumina Bound Zeolite Mordenite (Comparative)

One gram of alumina bound zeolite mordenite was used in testing DCHB/benzene transalkylation following the procedure described above. Product sampling started after 43 hours on stream and the results are shown in Table 1.

Example 3

DCHB/Benzene Transalkylation Over Alumina Bound MCM-22 (Comparative)

One gram of alumina bound zeolite MCM-22 was used in testing DCHB/benzene transalkylation following the procedures in Example 1. A product sample was taken after 67 hours on stream and the results are shown in Table 1.

Example 4

DCHB/Benzene Transalkylation Over Alumina Bound Zeolite Beta (Comparative)

One gram of alumina bound zeolite Beta was used in testing DCHB/benzene transalkylation following the procedure described above. A product sample was taken after 67 hours on stream and the results are shown in Table 1.

Example 5

DCHB/Benzene Transalkylation Over Alumina Bound Y (Comparative)

One gram of alumina bound zeolite Y ($Si/Al_2$=5.1; unit cell size of 24.52 Angstrom) was used in testing DCHB/benzene transalkylation following the procedure described above. A product sample was taken after 18 hours on stream and the results are shown in Table 1.

Example 6

DCHB/Benzene Transalkylation Over Alumina Bound High Si/Al Zeolite USY

One gram of alumina bound high silica/alumina molar ratio zeolite USY ($Si/Al_2$=60; unit cell size=24.26 Angstrom) was used in testing DCHB/benzene transalkylation following the procedure described above. A product sample was taken after 576 hours on stream and the results are shown in Table 1.

Example 7

DCHB/Benzene Transalkylation Over Alumina Bound High Si/Al Zeolite USY

One gram of alumina bound high silica/alumina molar ratio zeolite USY ($Si/Al_2$=60; unit cell size=24.26 Angstrom)

was used in testing DCHB/benzene transalkylation following the procedure described above, except the weight ratio of benzene/DCHB was 6/1 and the feed flow rate was 4.6 cc/h to achieve WHSV of 4 for the total feed. A product sample was taken after 576 hours on stream and the results are shown in Table 1.

The results in Table 1 clearly show that zeolite USY with high silica/alumina molar ratio and low unit cell has significant advantages over the other zeolite catalysts tested: DCHB conversion and cyclohexylbenzene (CHB) selectivity are high while MCPB and $C_{18}$+ selectivities are low. Increasing the benzene/DCHB weight ratio in the feed from 3 to 6 further increases selectivity to CHB (Example 7). A weight ratio of benzene to DCHB of 3 is approximately equal to a molar ratio of about 1. A weight ratio of benzene to DCHB is approximately equal to a molar ratio of about 2.

TABLE 1

| | Example | | | | | | |
|---|---|---|---|---|---|---|---|
| | 1 | 2 | 3 | 4 | 5 | 6 | 7 |
| Catalyst | WOx/ZrO$_2$ | Mordenite | MCM-22 | Beta | Y | High Si/Al USY | High Si/Al USY |
| Unit Cell size (Angstrom) | | | | | 24.52 | 24.26 | 24.26 |
| Alpha | | 565 | 560 | 350 | 49 | 43 | 43 |
| Binder | none | alumina | alumina | alumina | alumina | alumina | Alumina |
| Total BET Surface Area, m2/g | | 494 | 539 | | 587 | 669 | 669 |
| Zeolite Surface Area, m2/g | | 322 | 370 | | 489 | 543 | 543 |
| Matrix Surface Area, m2/g | | 172 | 169 | | 98 | 126 | 126 |
| Avg. Pore Size by N2 BET PSD (nm) | | 6.73 | 11.34 | | 8.05 | 5.75 | 5.75 |
| Pore Volume, cc/g | | 0.742 | | | 0.656 | 0.742 | 0.742 |
| Days on stream | 1.1 | 1.8 | 2.8 | 2.8 | 0.8 | 24 | 24 |
| Temperature (° C.) | 150 | 180 | 180 | 180 | 170 | 170 | 170 |
| DCHB conversion (%) | 63.0 | 79.3 | 16.0 | 47.0 | 36 | 56 | 63 |
| Selectivity (wt %) | | | | | | | |
| Lights | 0.227 | | 9.21 | 0.047 | 1.0 | | |
| Methylcyclopentane | 0.442 | 0.151 | 0.26 | 0.024 | 0.21 | 0.5 | 0.4 |
| Cyclohexane | 0.091 | 0.746 | 0.2 | 0.428 | | | |
| Toluene | 0.028 | | | 0.028 | | | |
| Methylcyclopentylbenzene | 1.609 | 22.45 | 3.85 | 5.85 | 7.03 | 0.8 | 1.2 |
| Other C$_{12}$ | | 1.51 | 3.38 | | | 0.4 | 0.1 |
| CHB | 96.64 | 69.95 | 62.92 | 92.77 | 92.12 | 94.4 | 97.5 |
| Other C$_{18}$ | 0.963 | 5.097 | 18.9 | 0.853 | | 2.7 | 0.7 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for the transalkylation of polycyclohexylbenzenes, the process comprising contacting a feed containing at least one polycyclohexylbenzene with benzene under transalkylation conditions with a transalkylation catalyst comprising a zeolite USY having a silica to alumina molar ratio in excess of 10 to convert at least part of said polycyclohexylbenzene to cyclohexylbenzene.

2. The process of claim 1, wherein the feed comprises at least part of an effluent produced by a method comprising contacting benzene and hydrogen under hydroalkylation conditions with a hydroalkylation catalyst comprising a hydrogenation metal and a molecular sieve selected from zeolite beta, zeolite X, zeolite Y, mordenite, MCM-68 and a molecular sieve of the MCM-22 family.

3. A process for producing cyclohexylbenzene, the process comprising:
   (a) contacting benzene and hydrogen with a hydroalkylation catalyst under hydroalkylation conditions to produce an effluent containing cyclohexylbenzene and a polycyclohexylbenzene;
   (b) separating cyclohexylbenzene from said effluent; and
   (c) reacting at least part of the polycyclohexylbenzene from said effluent with benzene under transalkylation conditions with a transalkylation catalyst comprising a zeolite USY having a silica to alumina molar ratio in excess of 10 to convert at least part of said polycyclohexylbenzene to cyclohexylbenzene.

4. The process of claim 3, wherein the hydroalkylation catalyst comprises a hydrogenation metal and a molecular sieve selected from zeolite beta, zeolite X, zeolite Y, mordenite, MCM-68 and a molecular sieve of the MCM-22 family.

5. A process for producing phenol and cyclohexanone, the process comprising:
   (a) producing cyclohexylbenzene by the process claimed in claim 3;
   (b) oxidizing at least part of the cyclohexylbenzene to produce cyclohexylbenzene hydroperoxide; and
   (c) cleaving at least part of the cyclohexylbenzene hydroperoxide to produce phenol and cyclohexanone.

6. The process of claim 3, wherein the zeolite USY of the transalkylation catalyst has a silica to alumina molar ratio in excess of 25.

7. The process of claim 3, wherein the zeolite USY of the transalkylation catalyst has a silica to alumina molar ratio in excess of 50.

8. The process of claim 3, wherein the zeolite USY of the transalkylation catalyst has a unit cell size less than or equal to 24.50.

9. The process of claim 3, wherein the transalkylation catalyst has an alpha value less than 100.

10. The process of claim 3, wherein the transalkylation catalyst includes an alumina binder.

11. The process of claim 3, wherein said transalkylation conditions comprise a temperature of 100° C. to 300° C., a pressure of 350 kPA to 4200 kPa, and a benzene to polycyclohexylbenzene molar ratio of 1:1 to 50:1.

12. The process of claim 3, wherein the polycyclohexylbenzene comprises di-cyclohexylbenzene.

13. The process of claim 3, wherein the polycyclohexylbenzene comprises tri-cyclohexylbenzene.

14. The process of claim 3, wherein the silica to alumina molar ratio is no greater than 1,000.

15. The process of claim 3, wherein the silica to alumina molar ratio is from 25 to 1,000.

16. The process of claim 8, wherein the zeolite USY of the transalkylation catalyst has a unit cell size less than or equal to 24.26.

* * * * *